United States Patent [19]
Goble et al.

[11] Patent Number: 6,027,501
[45] Date of Patent: Feb. 22, 2000

[54] ELECTROSURGICAL INSTRUMENT

[75] Inventors: Nigel Mark Goble, Cardiff; Colin Charles Owen Goble, Penarth, both of United Kingdom

[73] Assignee: Gyrus Medical Limited, Cardiff, United Kingdom

[21] Appl. No.: 08/737,302

[22] PCT Filed: Jun. 20, 1998

[86] PCT No.: PCT/GB96/01472

§ 371 Date: Oct. 26, 1996

§ 102(e) Date: Oct. 26, 1996

[87] PCT Pub. No.: WO97/00646

PCT Pub. Date: Jan. 9, 1997

[30] Foreign Application Priority Data

Jun. 23, 1995 [GB] United Kingdom .................... 9512889
Jan. 9, 1996 [GB] United Kingdom .................... 9600356

[51] Int. Cl.$^7$ .................................................. A61B 17/39
[52] U.S. Cl. .............................. 606/41; 606/45; 606/46; 606/48; 606/50; 607/101
[58] Field of Search ............................ 606/34, 37, 41–50, 606/22, 26; 607/100, 101, 119, 122

[56] References Cited

U.S. PATENT DOCUMENTS

| Re. 33,925 | 5/1992 | Bales et al. . |
|---|---|---|
| 164,184 | 6/1875 | Kidder . |
| 1,366,756 | 1/1921 | Wappler . |
| 1,735,271 | 11/1929 | Groff . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |
| 2,050,904 | 8/1936 | Trice . |
| 2,056,377 | 10/1936 | Wappler . |

(List continued on next page.)

FOREIGN PATENT DOCUMENTS

| 0 013605 | 7/1980 | European Pat. Off. . |
|---|---|---|
| 0 049633 | 4/1982 | European Pat. Off. . |
| 0 067680 | 12/1982 | European Pat. Off. . |
| 0 136855 | 4/1985 | European Pat. Off. . |
| 0 219568 | 12/1985 | European Pat. Off. . |
| 0 205 851 | 12/1986 | European Pat. Off. . |
| 0 280798 | 9/1988 | European Pat. Off. . |
| 0 310431 | 4/1989 | European Pat. Off. . |
| 0 316469 | 5/1989 | European Pat. Off. . |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

(List continued on next page.)

*Primary Examiner*—Linda C. M. Dvorak
*Assistant Examiner*—David M. Ruddy
*Attorney, Agent, or Firm*—Nixon & Vanderhye P.C.

[57] ABSTRACT

An electrosurgical instrument, which is used to treat tissue in the presence of an electrically-conductive fluid, comprises an instrument shaft and an electrode assembly at one end of the shaft. The electrode assembly comprises a tissue treatment electrode and a return electrode which is electrically insulated from the tissue treatment electrode by means of an insulation member. The tissue treatment electrode is exposed at the extreme distal end of the instrument, and the return electrode has a fluid contact surface spaced from the exposed end of the tissue treatment electrode by the insulation member. The instrument further comprises feed means for feeding electrically-conductive fluid to the region of the exposed end of the tissue treatment electrode in such a manner as to define, in use, a conductive fluid path that completes an electrical circuit between the tissue treatment and the return electrode.

37 Claims, 3 Drawing Sheets

U.S. PATENT DOCUMENTS

| | | |
|---|---|---|
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |
| 3,707,149 | 12/1972 | Hao et al. . |
| 3,801,766 | 4/1974 | Morrison, Jr. . |
| 3,815,604 | 6/1974 | O'Malley et al. . |
| 3,845,771 | 11/1974 | Vise . |
| 3,847,153 | 11/1974 | Weissman . |
| 3,870,047 | 3/1975 | Gonser . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. ............ 606/48 |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,520 | 4/1982 | Doss . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris et al. . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers et al. . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels . |
| 5,013,312 | 5/1991 | Parins et al. . |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker et al. . |
| 5,071,418 | 12/1991 | Rosenbaum . |
| 5,080,660 | 1/1992 | Beulna . |
| 5,083,565 | 1/1992 | Parins . |

| | | | | | |
|---|---|---|---|---|---|
| 5,085,659 | 2/1992 | Rydell . | 5,422,567 | 6/1995 | Matsunaga . |
| 5,088,997 | 2/1992 | Delahuerga et al. . | 5,423,808 | 6/1995 | Edwards et al. . |
| 5,098,431 | 3/1992 | Rydell . | 5,423,809 | 6/1995 | Klicek . |
| 5,099,840 | 3/1992 | Goble et al. . | 5,423,810 | 6/1995 | Goble et al. . |
| 5,108,391 | 4/1992 | Flachenecker et al. . | 5,423,811 | 6/1995 | Imran et al. . |
| 5,108,407 | 4/1992 | Geremia et al. . | 5,431,649 | 7/1995 | Mulier et al. . |
| 5,117,978 | 6/1992 | Blumenfeld et al. . | 5,437,662 | 8/1995 | Nardella ................................. 606/48 |
| 5,122,138 | 6/1992 | Manwaring . | 5,438,302 | 8/1995 | Goble . |
| 5,133,365 | 7/1992 | Heil, Jr. et al. . | 5,441,499 | 8/1995 | Fritzsch . |
| 5,158,561 | 10/1992 | Rydell et al. . | 5,443,470 | 8/1995 | Stern et al. . |
| 5,167,658 | 12/1992 | Ensslin . | 5,454,809 | 10/1995 | Janssen . |
| 5,167,659 | 12/1992 | Ohtomo . | 5,462,521 | 10/1995 | Brucker et al. . |
| 5,171,255 | 12/1992 | Rydell . | 5,472,441 | 12/1995 | Edwards et al. . |
| 5,171,311 | 12/1992 | Rydell et al. . | 5,472,443 | 12/1995 | Cordis et al. . |
| 5,178,620 | 1/1993 | Eggers et al. . | 5,480,397 | 1/1996 | Eggers et al. . |
| 5,190,517 | 3/1993 | Zieve et al. . | 5,480,398 | 1/1996 | Eggers et al. . |
| 5,195,959 | 3/1993 | Smith . | 5,496,312 | 3/1996 | Klicek . |
| 5,196,007 | 3/1993 | Ellman et al. . | 5,496,314 | 3/1996 | Eggers ..................................... 606/48 |
| 5,197,963 | 3/1993 | Parins . | 5,505,728 | 4/1996 | Ellman et al. . |
| 5,201,743 | 4/1993 | Haber et al. . | 5,505,730 | 4/1996 | Edwards . |
| 5,207,675 | 5/1993 | Canady . | 5,507,743 | 4/1996 | Edwards et al. . |
| 5,217,457 | 6/1993 | Delahuerga et al. . | 5,514,129 | 5/1996 | Smith . |
| 5,217,458 | 6/1993 | Parins . | 5,514,130 | 5/1996 | Baker . |
| 5,217,459 | 6/1993 | Kamerling ................................. 606/48 | 5,514,131 | 5/1996 | Edwards et al. . |
| 5,221,281 | 6/1993 | Klicek . | 5,520,684 | 5/1996 | Imran . |
| 5,244,462 | 9/1993 | Delahuerga et al. . | 5,520,685 | 5/1996 | Wojciechowicz . |
| 5,249,585 | 10/1993 | Turner et al. . | 5,522,815 | 6/1996 | Durgin, Jr. et al. . |
| 5,250,047 | 10/1993 | Rydell . | 5,531,744 | 7/1996 | Nardella et al. . |
| 5,258,006 | 11/1993 | Rydell et al. . | 5,536,267 | 7/1996 | Edwards et al. . |
| 5,259,395 | 11/1993 | Li . | 5,540,680 | 7/1996 | Guglielmi et al. . |
| 5,261,906 | 11/1993 | Pennino et al. . | 5,540,681 | 7/1996 | Strul et al. . |
| 5,267,994 | 12/1993 | Gentelia et al. . | 5,540,682 | 7/1996 | Gardner et al. . |
| 5,267,997 | 12/1993 | Farin et al. . | 5,540,683 | 7/1996 | Ichikawa et al. . |
| 5,277,201 | 1/1994 | Stern . | 5,540,684 | 7/1996 | Hassler, Jr. . |
| 5,277,696 | 1/1994 | Hagen ........................................ 606/50 | 5,540,685 | 7/1996 | Parins et al. . |
| 5,281,213 | 1/1994 | Milder et al. . | 5,542,916 | 8/1996 | Hirsch et al. . |
| 5,281,216 | 1/1994 | Klicek . | 5,542,945 | 8/1996 | Fritzsch . |
| 5,282,799 | 2/1994 | Rydell . | 5,545,161 | 8/1996 | Imran . |
| 5,282,845 | 2/1994 | Bush et al. . | 5,545,193 | 8/1996 | Fleischman et al. . |
| 5,290,282 | 3/1994 | Casscells . | 5,549,605 | 8/1996 | Hahnen . |
| 5,290,283 | 3/1994 | Suda . | 5,554,172 | 9/1996 | Horner et al. . |
| 5,300,068 | 4/1994 | Rosar . | 5,555,618 | 9/1996 | Winkler . |
| 5,300,069 | 4/1994 | Hunsberger . | 5,556,396 | 9/1996 | Cohen et al. . |
| 5,300,070 | 4/1994 | Gentelia et al. . | 5,556,397 | 9/1996 | Long et al. . |
| 5,304,214 | 4/1994 | DeFord et al. . | 5,558,671 | 9/1996 | Yates . |
| 5,306,238 | 4/1994 | Fleenor . | 5,562,720 | 10/1996 | Stern et al. . |
| 5,317,155 | 5/1994 | King . | 5,569,164 | 10/1996 | Lurz . |
| 5,318,563 | 6/1994 | Malis et al. . | 5,569,242 | 10/1996 | Lax et al. . |
| 5,320,627 | 6/1994 | Sorensen et al. . | 5,569,244 | 10/1996 | Hahnen . |
| 5,330,470 | 7/1994 | Hagen . | 5,569,245 | 10/1996 | Guglielmi et al. . |
| 5,330,471 | 7/1994 | Eggers . | 5,575,789 | 11/1996 | Bell et al. . |
| 5,334,193 | 8/1994 | Nardella . | 5,578,007 | 11/1996 | Imran . |
| 5,334,198 | 8/1994 | Hart et al. . | 5,582,609 | 12/1996 | Swanson et al. . |
| 5,336,222 | 8/1994 | Durgin, Jr. et al. . | 5,582,610 | 12/1996 | Grossi et al. . |
| 5,342,357 | 8/1994 | Nardella . | 5,584,830 | 12/1996 | Ladd et al. . |
| 5,342,391 | 8/1994 | Foshee et al. . | 5,591,141 | 1/1997 | Nettekoven . |
| 5,344,428 | 9/1994 | Griffiths . | 5,599,344 | 2/1997 | Paterson . |
| 5,352,222 | 10/1994 | Rydell . | 5,599,345 | 2/1997 | Edwards et al. . |
| 5,354,296 | 10/1994 | Turkel . | 5,599,346 | 2/1997 | Edwards et al. . |
| 5,366,443 | 11/1994 | Eggers et al. . | 5,599,347 | 2/1997 | Hart et al. . |
| 5,370,645 | 12/1994 | Klicek et al. . | 5,599,348 | 2/1997 | Gentelia et al. . |
| 5,370,675 | 12/1994 | Edwards et al. . | 5,599,349 | 2/1997 | D'Amelio . |
| 5,372,596 | 12/1994 | Klicek et al. . | 5,603,711 | 2/1997 | Parins et al. . |
| 5,382,247 | 1/1995 | Cimino et al. . | 5,603,712 | 2/1997 | Koranda et al. . |
| 5,383,874 | 1/1995 | Jackson et al. . | 5,607,422 | 3/1997 | Smeets et al. . |
| 5,383,876 | 1/1995 | Nardella . | 5,609,151 | 3/1997 | Mulier et al. . |
| 5,383,917 | 1/1995 | Desai et al. . | 5,609,573 | 3/1997 | Sandock . |
| 5,383,923 | 1/1995 | Webster, Jr. . | 5,611,798 | 3/1997 | Eggers . |
| 5,395,363 | 3/1995 | Billings et al. . | 5,620,481 | 4/1997 | Desai et al. . |
| 5,395,368 | 3/1995 | Ellman et al. . | 5,624,439 | 4/1997 | Edwards et al. . |
| 5,403,311 | 4/1995 | Abele et al. ................................ 606/48 | 5,626,560 | 5/1997 | Soring . |
| 5,419,767 | 5/1995 | Eggers et al. . | 5,626,575 | 5/1997 | Crenner . |

| | | |
|---|---|---|
| 5,626,576 | 5/1997 | Janssen . |
| 5,626,578 | 5/1997 | Tihon . |
| 5,628,745 | 5/1997 | Bek . |
| 5,628,771 | 5/1997 | Mizukawa et al. . |
| 5,630,426 | 5/1997 | Eggers et al. . |
| 5,633,578 | 5/1997 | Eggers et al. . |
| 5,634,924 | 6/1997 | Turkel et al. . |
| 5,672,174 | 9/1997 | Gough et al. . |
| 5,683,366 | 11/1997 | Eggers et al. . |
| 5,693,045 | 12/1997 | Eggers . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,700,262 | 12/1997 | Acosta et al. . |
| 5,725,524 | 3/1998 | Mulier et al. . |
| 5,766,153 | 6/1998 | Eggers et al. . |
| 5,810,764 | 9/1998 | Eggers et al. . |
| 5,833,689 | 11/1998 | Long . |
| 5,843,019 | 12/1998 | Eggers et al. . |
| 5,860,951 | 1/1999 | Eggers et al. . |
| 5,871,469 | 2/1999 | Eggers et al. . |
| 5,873,855 | 2/1999 | Eggers et al. . |
| 5,888,198 | 3/1999 | Eggers et al. . |
| 5,891,095 | 4/1999 | Eggers et al. . |
| 5,902,272 | 5/1999 | Eggers et al. . |

FOREIGN PATENT DOCUMENTS

| | | |
|---|---|---|
| 0 325456 | 7/1989 | European Pat. Off. . |
| 0 3323308 | 9/1989 | European Pat. Off. . |
| 0 373670 | 6/1990 | European Pat. Off. . |
| 0 392 837 | 10/1990 | European Pat. Off. . |
| 0 407057 | 1/1991 | European Pat. Off. . |
| 0 412426 | 2/1991 | European Pat. Off. . |
| 0 437377 | 7/1991 | European Pat. Off. . |
| 0 448798 | 10/1991 | European Pat. Off. . |
| 0 499491 | 8/1992 | European Pat. Off. . |
| 0 507622 | 10/1992 | European Pat. Off. . |
| 0 509670 | 10/1992 | European Pat. Off. . |
| 0 517243 | 12/1992 | European Pat. Off. . |
| 0 518230 | 12/1992 | European Pat. Off. . |
| 0 530400 | 3/1993 | European Pat. Off. . |
| 0 536440 | 4/1993 | European Pat. Off. . |
| 0 558316 | 9/1993 | European Pat. Off. . |
| 0 558318 | 9/1993 | European Pat. Off. . |
| 0 647435 | 4/1995 | European Pat. Off. . |
| 0 653192 | 5/1995 | European Pat. Off. . |
| 0 674909 | 10/1995 | European Pat. Off. . |
| 0 684015 | 11/1995 | European Pat. Off. . |
| 0 688536 | 12/1995 | European Pat. Off. . |
| 0 692224 | 1/1996 | European Pat. Off. . |
| 0 694290 | 1/1996 | European Pat. Off. . |
| 0 697199 | 2/1996 | European Pat. Off. . |
| 0 709065 | 5/1996 | European Pat. Off. . |
| 0 714635 | 6/1996 | European Pat. Off. . |
| 0 717967 | 6/1996 | European Pat. Off. . |
| 0 732080 | 9/1996 | European Pat. Off. . |
| 0 733345 | 9/1996 | European Pat. Off. . |
| 0 737447 | 10/1996 | European Pat. Off. . |
| 57862 | 9/1953 | France . |
| 1215305 | 4/1960 | France . |
| 1454773 | 10/1966 | France . |
| 2313949 | 1/1977 | France . |
| 2443829 | 7/1980 | France . |
| 2501034 | 9/1982 | France . |
| 651428 | 9/1937 | Germany . |
| 1007960 | 5/1957 | Germany . |
| 2222820 | 11/1973 | Germany . |
| 2457900 | 5/1976 | Germany . |
| 2930982 | 2/1981 | Germany . |
| 3209444 | 10/1982 | Germany . |
| 3215832 | 11/1982 | Germany . |
| 3119735 | 1/1983 | Germany . |
| 3245570 | 6/1984 | Germany . |
| 222 207 | 5/1985 | Germany . |
| 3423356 | 1/1986 | Germany . |
| 3427517 | 1/1986 | Germany . |
| 3511107 | 10/1986 | Germany . |
| 3623688 | 1/1987 | Germany . |
| 3530335 | 3/1987 | Germany . |
| 3707820 | 9/1987 | Germany . |
| 3622337 C2 | 1/1988 | Germany . |
| 3642077 C2 | 6/1988 | Germany . |
| 3708801 C2 | 9/1988 | Germany . |
| 3824913 | 2/1990 | Germany . |
| 3838840 C2 | 5/1990 | Germany . |
| 3930451 | 3/1991 | Germany . |
| 4108269 C2 | 6/1992 | Germany . |
| 4103972 C2 | 8/1992 | Germany . |
| 4126608 | 2/1993 | Germany . |
| 4139029 C2 | 6/1993 | Germany . |
| 4217999 A1 | 12/1993 | Germany . |
| 4237321 A1 | 5/1994 | Germany . |
| 4323585 | 1/1995 | Germany . |
| 4339049 | 5/1995 | Germany . |
| 44 25 015 | 1/1996 | Germany . |
| 19530004 | 3/1996 | Germany . |
| 4429478 | 3/1996 | Germany . |
| 19510185 | 10/1996 | Germany . |
| 19512640 C2 | 10/1996 | Germany . |
| 19514553 C1 | 10/1996 | Germany . |
| 62-211060 | 9/1987 | Japan . |
| 644491 | 1/1979 | Russian Federation . |
| 243478 | 7/1946 | Switzerland . |
| 1361497 | 7/1974 | United Kingdom . |
| 2037167 | 7/1980 | United Kingdom . |
| 1583397 | 1/1981 | United Kingdom . |
| 2133290 | 7/1984 | United Kingdom . |
| 2145932 | 4/1985 | United Kingdom . |
| 2161081 | 1/1986 | United Kingdom . |
| 2164473 | 3/1986 | United Kingdom . |
| 2177309 | 1/1987 | United Kingdom . |
| 2179861 | 3/1987 | United Kingdom . |
| 2213381 | 8/1989 | United Kingdom . |
| 2214430 | 9/1989 | United Kingdom . |
| WO 81/03271 | 11/1981 | WIPO . |
| WO 82/00084 | 1/1982 | WIPO . |
| WO 82/02488 | 8/1982 | WIPO . |
| WO 84/03829 | 10/1984 | WIPO . |
| WO 88/01851 | 3/1988 | WIPO . |
| WO 90/03152 | 4/1990 | WIPO . |
| WO 93/08756 | 5/1993 | WIPO . |
| WO 93/13718 | 7/1993 | WIPO . |
| WO 93/13816 | 7/1993 | WIPO . |
| WO 93/16650 | 9/1993 | WIPO . |
| WO 93/19681 | 10/1993 | WIPO . |
| WO 93/19682 | 10/1993 | WIPO . |
| WO 93/20747 | 10/1993 | WIPO . |
| WO 93/20877 | 10/1993 | WIPO . |
| WO 94/04220 | 3/1994 | WIPO . |
| WO 94/06510 | 3/1994 | WIPO . |
| WO 94/10921 | 5/1994 | WIPO . |
| WO 94/10924 | 5/1994 | WIPO . |
| WO 94/10925 | 5/1994 | WIPO . |
| WO 94/23659 | 10/1994 | WIPO . |
| WO 94/26228 | 11/1994 | WIPO . |
| WO 94/28809 | 12/1994 | WIPO . |
| WO 95/02369 | 1/1995 | WIPO . |
| WO 95/05781 | 3/1995 | WIPO . |
| WO 95/09576 | 4/1995 | WIPO . |
| WO 95/09577 | 4/1995 | WIPO . |
| WO 95/10320 | 4/1995 | WIPO . |
| WO 95/10321 | 4/1995 | WIPO . |
| WO 95/17855 | 7/1995 | WIPO . |

| | | |
|---|---|---|
| WO 95/18575 | 7/1995 | WIPO . |
| WO 95/19733 | 7/1995 | WIPO . |
| WO 95/20360 | 8/1995 | WIPO . |
| WO 95/23558 | 9/1995 | WIPO . |
| WO 95/24160 | 9/1995 | WIPO . |
| WO 95/25472 | 9/1995 | WIPO . |
| WO 95/26686 | 10/1995 | WIPO . |
| WO 95/30377 | 11/1995 | WIPO . |
| WO 96/00036 | 1/1996 | WIPO . |
| WO 96/00039 | 1/1996 | WIPO . |
| WO 96/00040 | 1/1996 | WIPO . |
| WO 96/00042 | 1/1996 | WIPO . |
| WO 96/00043 | 1/1996 | WIPO . |
| WO 96/00528 | 1/1996 | WIPO . |
| WO 96/04859 | 2/1996 | WIPO . |
| WO 96/07360 | 3/1996 | WIPO . |
| WO 96/09010 | 3/1996 | WIPO . |
| WO 96/10367 | 4/1996 | WIPO . |
| WO 96/14020 | 5/1996 | WIPO . |
| WO 96/14021 | 5/1996 | WIPO . |
| WO 96/18349 | 6/1996 | WIPO . |
| WO 96/19152 | 6/1996 | WIPO . |
| WO 96/23448 | 8/1996 | WIPO . |
| WO 96/23449 | 8/1996 | WIPO . |
| WO 96/24296 | 8/1996 | WIPO . |
| WO 96/24301 | 8/1996 | WIPO . |
| WO 96/27337 | 9/1996 | WIPO . |
| WO 96/29946 | 10/1996 | WIPO . |
| WO 95/31144 | 11/1998 | WIPO . |

OTHER PUBLICATIONS

Wyeth, G.A., *Electrosurgical Unit*, pp. 1180–1202.

Everest Medical Technologies, Inc., "Everest Bipolar Laparascopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., "A Bipolar Electrosurgical TURP Loop,"Abstract of Paper P14–11, 7$^{th}$ World Congress on Endourology and ESWL, Nov. 27–30, Kyoto, Japan, 1989, p. 248.

Ramsay, J.W.A. et al., "A Comparison of Bipolar and Monopolar Diathermy Probes in Experimental Animals," Urological Research, Springer–Verlag 1985, 13:99–102.

German Article w/Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulaton: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator —Some Underlying Principles and Results," Archives of Surgery, vol. 18, 1929, pp. 1863–1873.

McLean, A. J., "Characteristics of Adequate Electrosurgical Current," American Journal of Surgery, vol. XVII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, $2_{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Elecrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint from Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgry: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents —With Illustrative Cases*, CRC Press, New York, 1998, p. 93 (commentary on Honig, William M., "The Mechanism of Cutting in Electrosurgery," IEEE Transactions on Biomedical Engineering, Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

ELECTROSURGICAL INSTRUMENT

BACKGROUND OF THE INVENTION

This invention relates to an electrosurgical instrument for the treatment of tissue in the presence of an electrically conductive fluid medium, to electrosurgical apparatus including such an instrument, and to an electrode unit for use in such an instrument.

Endoscopic electrosurgery is useful for treating tissue in cavities of the body, and is normally performed in the presence of a distension medium. When the distension medium is a liquid, the technique is commonly referred to as underwater electrosurgery, this turn denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin in a position remote from the operating site. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the casse of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

When performing surgery in body cavities, vital structures often lie in close proximity to the site of application, and these structures may be damaged by the collateral spread of the electrosurgical effect. Also of concern when using monopolar electrosurgery is that the operating voltage is elevated to overcome the resistive current limiting of the patient's tissues or to overcome carbonisation of the application electrode. Arcing by direct coupling to adjacent structures, or through breaches in insulation, may produce accidental tissue damage outside the narrow field of view of the endoscope. There is also the risk of capacitive coupling between the instrument and the patient's tissues at the entry point into the body cavity such that electrosurgical energy may be coupled to tissue at the entry point. This coupled energy can sometimes be sufficient to cause burning These risks of using monopolar electrosurgery during endoscopic procedures are now well recognised, and have driven a move towards adoption of bipolar surgery.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure correct contact of both electrodes with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrodes.

The electrical junction between the return electrode and the tissue can be supported by wetting of the tissue by a conductive solution such as normal saline. Both monopolar and bipolar probe arrangements often provide a means of suction and irrigation, primarily intended to wash the operative site. In such a case, the active electrode is retracted within the irrigation sheath to enable direct contact of the sheath with the tissue without the risk of mechanical damage to the tissue by the exposed electrode. No surgical effect can be produced with the electrode retracted, or during the passage of saline. As a secondary benefit, this arrangement allows the wetting of tissue to reduce contact impedance.

In bipolar needle arrangements, one of the obvious limitations is that the active electrode must be completely buried in the tissue to enable the return electrode to complete the circuit. Another problem is one of orientation: even a relatively small change in application angle from the ideal perpendicular contact with respect to the tissue surface, will change the electrode contact area ratio, so that a surgical effect can occur in the tissue contacting the return electrode.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of the applicants' co-pending British Patent Application No. 9512889.8.

The electrode structure of this instrument, in combination with a conductive distension medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangements.

This type of electrosurgical instrument is designed primarily for use in a saline environment, and so cannot be used in open air or gas-filled operating environments.

The aim of the invention is to provide an irrigated bipolar electrosurgical instrument that can be used in open air or gas-filled environments, in body fluids, or by insertion into tissue by the creation of a conductive fluid environment around the tip of the instrument.

SUMMARY OF THE INVENTION

The present invention provides an electrosurgical instrument for the treatment of tissue in the presence of an electrically-conductive fluid, the instrument comprising an instrument shaft and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a fluid contact surface spaced from the exposed end of the tissue treatment electrode by the insulation member, wherein the instrument further comprises feed means for feeding electrically-conductive fluid to the region of the exposed end of the tissue treatment electrode in such a manner as to define a conductive fluid path that completes, in use, an electrical circuit between the tissue treatment electrode and the return electrode.

In this way, it is possible to create a local conductive fluid environment around the tip of an electrosurgical instrument by delivering the fluid through the instrument in such a manner that the return electrode can be positioned remote from the tissue treatment electrode on or within the shaft of the instrument.

The electrode structure of this instrument thus simulates a monopolar configuration, with one active (tissue treatment) electrode and a remote return electrode, the return electrode being positioned on the instrument shaft to provide all the safety advantages of bipolar electrosurgery without the drawbacks. The separation of the two electrodes is supported by the delivery of the conductive medium, and allows higher powers to be delivered compared to conventional bipolar electrosurgery, but yet at power levels lower than conventional monopolar electrosurgery. The arrangement can also produce a contact vaporisation of tissue comparable to that of laser surgery.

The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid.

The electrosurgical instrument of the invention is useful for dissection, resection, vaporisation, dessication and coagulation of tissue and combinations of these functions with particular application in laparascopic, colposcopic (including vaginal speculum) and open surgical procedures on the female genital tract and adnexal related diseases. Laparascopic operative procedures may include: removal of subserosal and pedunculated fibroids, ablation of ectopic endometrium, ovarian cystectomy and ovarian drilling procedures; oophorectomy, salpingo-oophorectomy, subtotal hysterectomy and laparaoscopically assisted vaginal hysterectomy (LAVH) as may be performed for benign or malignant diseases; laparoscopic uterosacral nerve ablation (LUNA); fallopian tube surgery as correction of ectopic pregnancy or complications arising from acquired obstructions; division of abdominal adhesions; and haemostasis.

The electrosurgical instrument of the invention is also useful in the lower female genital tract, including treatment of cervix, vagina and external genitalia whether accessed directly or using instrumentation comprising generally speculae and colposcopes. Such applications include: vaginal hysterectomy and other pelvic procedures utilising vaginal access; LLETZ/LEEP procedure (large loop excision of the transformation zone) or excision of the transformation zone of the endocervix; removal of cystic or septic lesions; ablation of genital or venereal warts; excision of benign and malignant lesions; cosmetic and surgical repairs including vaginal prolapse; excision of diseased tissue; and haemostasis.

The electrosurgical instrument of the invention is also useful for dissection, resection, vaporisation, desiccation and coagulation of tissue and combinations of these functions with particular application in surgery on the ear nose and throat (ENT) and more particularly procedures performed on the oropharynx, nasopharynx and sinuses. These procedures may be performed through the mouth or nose using speculae or gags or using endoscopic techniques such as functional endoscopic sinus surgery (FESS). Functional endoscopic sinus procedures may include: removal of chronically-diseased, inflamed and hypertrophic mucus linings, polyps and neoplasms from the various anatomical sinuses of the skull; excision of diseased tissue; and haemostasis. Procedures on the nasopharynx may include: removal of chronically-diseased, inflamed and hypertrophic mucus linings, polyps and neoplasms from the turbinates and nasal passages; submucus resection of the nasal septum; excision of diseased tissue; and haemostasis. Procedures on the oropharynx may include: removal of chronically-diseased, inflamed and hypertrophic tissue, polyps and neoplasms particularly as they occur related to the tonsil, adenoid, epi-glottic and supra-glottic regions, and salivary glands; as an alternative method to perform the procedure commonly known as laser assisted uvulopalatoplasty (LAUP); excision of diseased tissue; and haemostasis.

It is evident from the scope of applications of the invention that it has further additional applications for dissection, resection, vaporisation, desiccation and coagulation of tissue and combinations of these functions in general lapaaroscopic, thoracoscopic and neurosurgical procedures, being particularly useful in the removal of diseased tissue and neoplastic disease whether benign or malignant.

Surgical procedures using the electrosurgical instrument of the invention include introducing the electrode assembly to the surgical site whether through an artificial (cannula) or natural conduit which may be in an anatomical body cavity or space or one created surgically either using the instrument itself or by another technique. The cavity or space may be distended during the procedure using a fluid, or may be naturally held open by anatomical structures. The surgical site may be bathed in a continuous flow of conductive fluid, such as saline solution, to create a locally-irrigated environment around the tip of the electrode assembly in a gas-filled cavity or on an external body surface or other such tissue surfaces exposed during part of a surgical procedure. The irrigating fluid may be aspirated from the surgical site to remove products created by application of the RF energy, tissue debris or blood. The procedures may include simultaneous viewing of the site via an endoscope or using an indirect visualisation means.

In a preferred embodiment, the instrument further comprises removal means for removing electrically conductive fluid from the region of the exposed end of the tissue treatment electrode. The removal means is particularly important when the conductive fluid is a liquid such as saline, as saline heated up by the electrosurgical output needs to be removed to prevent the risk of collateral tissue damage.

By continually feeding electrically-conductive fluid such as saline to the region of the tissue treatment (active) electrode, and continually removing the fluid from this region, it is possible to create a local fluid field at the active electrode. Moreover, as fluid is constantly replenished in this region, the temperature of the active electrode can be maintained at a desired level.

Advantageously, the removal means is constituted by a fluid return channel formed within the instrument shaft, and by means for applying suction to the proximal end of the fluid return channel, and the feed means is constituted by a fluid feed channel formed within the instrument shaft. The fluid feed channel may be positioned around the fluid return channel.

In a preferred embodiment, the return electrode is a tubular member which is coated with an insulating sheath, the coated return electrode constituting the instrument shaft. Advantageously, the inner surface of the tubular member constitutes the return electrode. Preferably, the tubular member is made of stainless steel. In this case, the tissue treatment electrode may be supported centrally within the tubular member by an insulating spacer. Conveniently, the insulating spacer is made of a ceramic material, silicone rubber or glass.

The instrument may further comprise a tube extending proximally of the spacer. Preferably, the feed channel is constituted by the annular space between the return electrode and the tube, and the return channel is constituted by the interior of the tube and aperture means extending through the spacer.

Alternatively, the instrument may further comprise a second return electrode constituted by a second tubular stainless steel member positioned concentrically within the first-mentioned tubular stainless steel member. In this case, the feed channel may be constituted by the annular space between the two return electrodes, and the return channel is constituted by the annular space between the second return electrode and the tube.

The invention also provides elecrosurgical apparatus comprising a radio frequency generator and an electrosurgical instrument for treatment of tissue in the presence of an electrically-conductive fluid medium, wherein the electrosurgical instrument is as defined above.

Advantageously, the radio frequency generator includes control means for varying the output power delivered to the electrodes, the control means being such as to provide output power in first and second output ranges, the first output range being for powering the electrosurgical instrument for tissue desiccation, and the second output range being for powering the electrosurgical instrument for tissue removal by cutting or vaporisation. Prefereably, the first output range is from about 150 volts to 200 volts, and the second output range is from about 250 volts to 600 volts, the voltages being peak voltages.

The invention further provides a method of operating an electrosurgical apparatus having at least at tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at the extreme distal end of the assembly, the return electrode having a fluid contact surface spaced from the exposed end of the tissue treatment electrode by the insulation member, the method comprising the steps of:

feeding electrically-conductive fluid to the region of the exposed end of the tissue treatment electrode; and controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode.

Advantageously, the method further comprises the step of removing electrically-conductive fluid from the region of the exposed end of the tissue treatment electrode.

The invention still further provides an electrosurgical tissue desiccation method comprising the steps of:

providing an electrosurgical apparatus comprising a radio frequency generator coupled to an electrode assembly comprising a tissue treatment electrode and a return electrode, the tissue treatment electrode having an exposed distal end;

introducing the electrode assembly into a selected operation site with the tissue treatment electrode adjacent to the tissue to be treated;

feeding electrically-conductive fluid to the region of the exposed end of the tissue treatment electrode;

actuating the generator; and controlling the radio frequency power supplied to the electrode assembly by the generator to maintain the conductive fluid adjacent to the tissue treatment electrode substantially at its boiling point without creating a vapour pocket surrounding the tissue treatment electrode.

In this case, the return electrode may be spaced proximally with respect to the tissue treatment electrode, and the electrode assembly may be introduced into the selected operation site such that the tissue treatment electrode is in contact with the tissue to be treated, and the return electrode is immersed in the electrically-conductive fluid, the electrode assembly being manipulated to cause heating and desiccation of the tissue in a required region adjacent to the tissue treatment electrode. Preferably, the electrode assembly is manipulated by moving the tissue treatment electrode across the surface of the tissue to be treated in a side-to-side "painting" technique.

The invention also provides an electrosurgical method comprising the steps of:

providing an electrosurgical apparatus comprising a radio frequency generator coupled to an electrode assembly comprising a tissue treatment electrode and a return electrode, the tissue treatment electrode having an exposed distal end;

introducing the electrode assembly into a selected operation site with the tissue contact electrode adjacent to the tissue to be treated;

feeling electrically-conductive fluid to the region of the exposed end of the tissue treatment electrode;

actuating the generator; and applying sufficient radio frequency power to the electrode assembly to vaporise the electrically-conductive fluid surrounding the tissue treatment electrode to maintain a vapour pocket surrounding the tissue treatment electrode.

Advantageously, the return electrode is spaced proximally with respect to the tissue treatment electrode, and the electrode assembly is introduced into the selected operation site such that the tissue treatment electrode is positioned at least adjacent to the tissue to be treated, with the vapour pocket in contact with the tissue, and with the return electrode in contact with the electrically conductive fluid, the electrode structure being manipulated to achieve at least vaporisation of the tissue.

BRIEF DESCRIPTION OF THE DRAWINGS

The invention will now be described in greater detail, by way of example, with reference to the drawings, in which:-

DETAILED DESCRIPTION OF PREFERRED EMBODIMENT

Each of the electrosurgical instruments described below is intended to be used with a conductive medium such as normal saline or argon. Each instrument has a dual-electrode structure, with the conductive medium acting as a conductor between the tissue being treated and one of the electrodes, hereinafter called the return electrode. The other electrode is applied directly, or immediately adjacent, to the tissue, and is hereinafter called the tissue treatment (active) electrode. In many cases, use of a liquid medium is preferable, as it prevents excessive electrode temperature in most circumstances, and largely eliminates tissue sticking.

Figure 1:
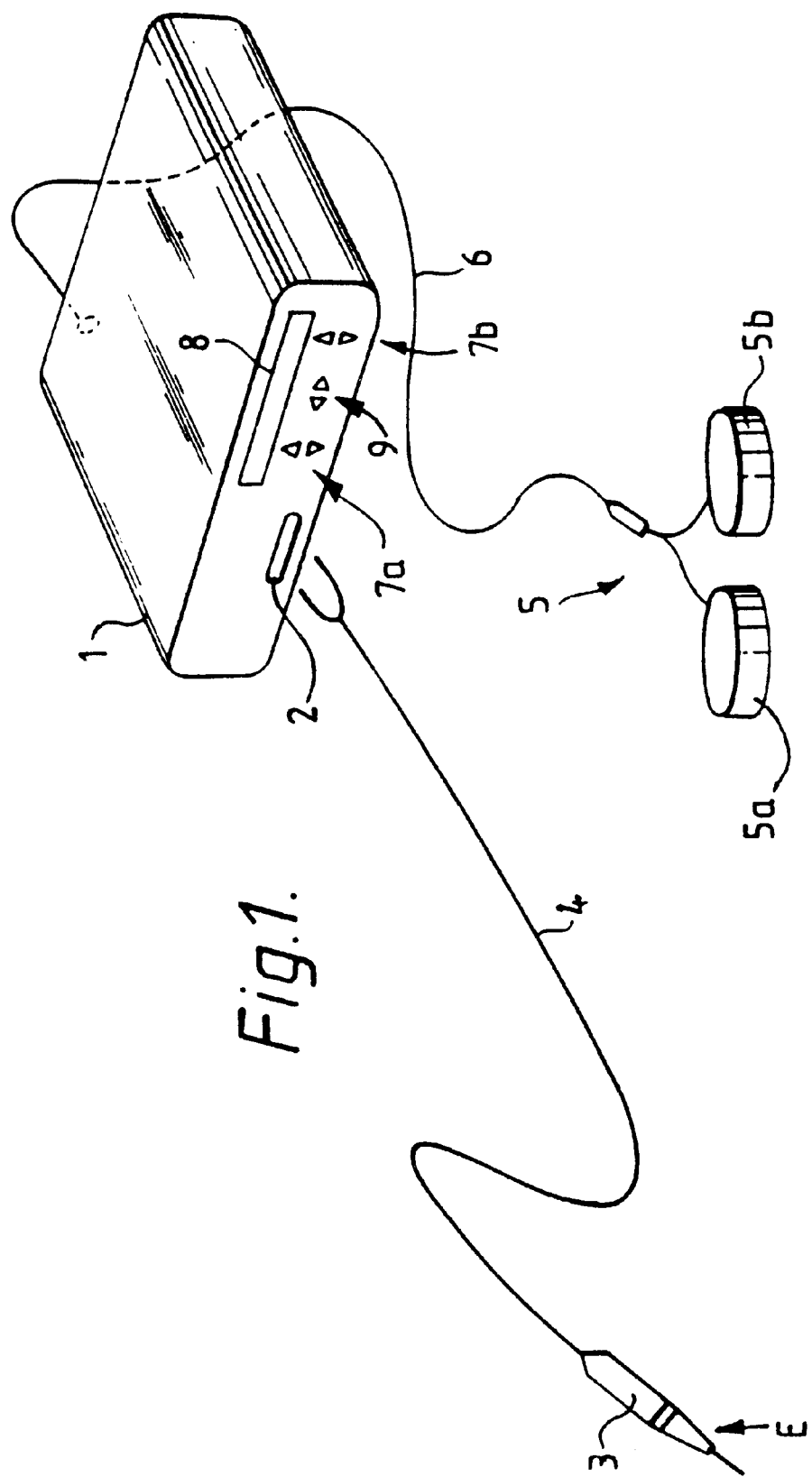
FIG. 1 is a diagram showing an electrosurgical apparatus constructed in accordance with the invention.

Referring to the drawings, FIG. 1 shows electrosurgical apparatus including a generator 1 having an output socket 2 providing a radio frequency (RF) output for an instrument in the form of a handpiece 3 via a connection cord 4. Activation of the generator 1 may be performed from the handpiece 3 via a control connection in the cord 4, or by means of a footswitch unit 5, as shown, connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9a are provided as an alternative means for selection between the desiccation and vaporiation modes.

The handpiece 3 mounts a detachable electrosurgical instrument E, such as the electrode units E1 and E2 to be described below.

Figure 2:
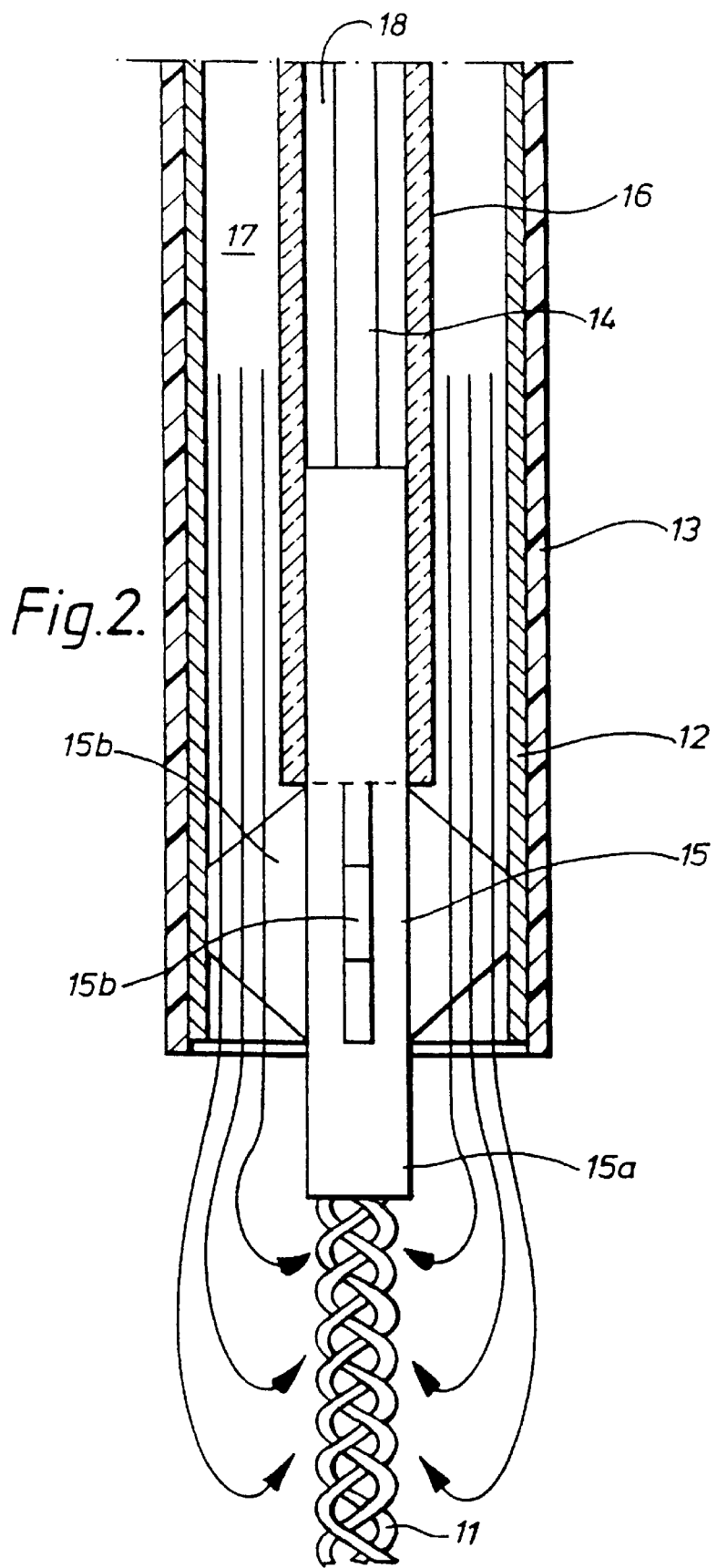
FIG. 2 is a schematic longitudinal sectional view of the distal end of a first form of electrosurgical instrument for use with the apparatus of FIG. 1.

FIG. 2 shows the distal end of the first form of the electrosurgical instrument E1. The instrument E1 is formed with an electrode assembly at the distal end thereof, the electrode assembly comprising a central tissue treatment (active) electrode 11 and a tubular return electrode 12. The active electrode 11 is made of twisted noble metal (such as platinum/iridium or platinum/tungsten), and the return electrode is a stainless steel tube. The return electrode 12 is completely enveloped by a polyimide insulating sheath 13. The return electrode 12 extends the entire length of the electrosurgical instrument El, and constitutes the shaft of the instrument.

The electrodes 11 and 12 are provided with current from the radio frequency (RF) generator 1 (not shown in FIG. 2), the return electrode 12 being directly connected to the generator and the active electrode 11 being connected via a copper conductor 14. The generator 1 may be as described in the specification of our co-pending British Patent Application No. 9604770.9. The active electrode 11 is held centrally within the return electrode 12 by means of a ceramic insulator/spacer 15. The insulator/spacer 15 has a generally cylindrical portion 15a surrounding the junction between the active electrode 11 and the conductor 14 and the adjacent regions of these two members, and four radially-extending, equispaced wings 15b which contact the internal circumferential wall of the return electrode 12 to hold the insulator/spacer, and hence the active electrode 11, centrally within the return electrode.

A tube 16, made of an insulating material such as PTFE, is a friction fit around the proximal end of the cylindrical portion 15a of the insulator/spacer 15, and extends substantially along the entire length of the instrument. The tube 16 defines, together with the return electrode 12, a coaxial saline supply channel 17, the interior of the tube 16 defining a saline return channel 18. In use, saline is fed to the channel 17 under gravity (no pumping being required), and saline is removed via the channel 18 and apertures (not shown) in the cylindrical portion 15a of the insulator/spacer 15 by means of suction. Preferably, the suction is carried out by a low noise pump (not shown) such as a moving vane pump or a diaphragm pump, rather than by using a high speed impeller. As the tubing leading to the pump will intermittently contain small quantities of saline, a large vacuum (at least 500 mBar) is required. However, the quantity of gas and liquid to be removed is comparatively small, and this permits the use of a moving vane or diaphragm pump, although a high volume peristaltic pump could also be used.

To circumvent the requirement for pump sterilisation, the pump operates via a disposable fluid trap (not shown) incorporating a 10 μm PTFE filter. This filter prevents both exhausted fluids and gas particulates from being drawn in by the pump and contaminating its workings and the surrounding environment.

The instrument E1 described above is intended for use in open air or gas filled environments, in body fluids, or by insertion into tissue by the creation of a conductive fluid environment around the tip of the instrument; and it is so arranged that it is possible to create a local saline field at a distal end of the instrument. This instrument E1 can, therefore, be used for laparoscopic applications. In use, saline is fed to the active electrode 11 via the channel 17, the saline providing a conductive medium to act as a conductive path between the tissue being treated and the return electrode 12. By varying the output of the generator 1, the instrument can be used for tissue removal by vaporisation, for cutting or for desiccation. In each case, as saline contacts the active electrode 11, it heats up until it reaches an equilibrium temperature dependent upon the power output of the generator 1 and the flow rate of the saline. In equilibrium, as fresh saline is fed via the channel 17 to the active electrode 11, the exterior temperature of the shaft is maintained at the same temperature as of that of the surrounding saline. As the insulating sheath 13 completely covers the external surface of the return electrode 12, accidental contact between the return electrode and tissue is avoided.

One of the advantages of using a low saline flow rate, is that the saline temperature can reach boiling point. However, as there is a continuous flow of saline, there is a temperature gradient rise in the saline from the return electrode 12 to the active electrode 11. This temperature gradient is important, as the hotter saline adjacent to the active electrode 11 reduces the power threshold requirement to reach vaporisation. Although the flow rate requirement can be calculated on the basis of the input power, the flexibility of the generator 1 in maintaining optimum power density means that the flow rate is non-critical. For example, if the generator is set for 100 W, then the maximum flow rate is theoretically calculated as follows:

$$\begin{aligned}
\text{Flow rate} &= \text{power/specific heat capacity} \\
&= 100/4.2 \times 75 \text{ cc/s} \\
&= 0.32 \text{ cc/s} \\
&= 19 \text{ cc/min}
\end{aligned}$$

This assumes an initial saline temperature of 25° C., and a heat capacity of 4200 J/kg/° C.

Although during vaporisation saline is brought into the vapour state, the vapour is only stable around the active electrode 11. Thus, the energy absorbed by virtue of the latent heat of vaporisation can be ignored, as this energy is recovered by freshly-arriving saline.

Another important factor is that, due to the very short circuit path of the saline, the current may be regarded as flowing along a number of different paths, which, therefore, do not have the same power density. Consequently, vaporisation can occur at flow rates higher than the calculated maximum, due to the unequal power densities within the saline environment. However, the amount of vaporisation occurring along the length of the active electrode 11 will depend upon the flow rate.

As the saline is heated up by the active electrode 11, it is potentially damaging to tissue as it can cause thermal necrosis. It is important, therefore, that all the heated saline is recovered and exhausted from the patient before coming into contact with the tissue adjacent to the application site. It is for this reason that there is suction from the active electrode 11 to an exhaust reservoir (not shown). However, by ensuring that the suction occurs in excess, no saline can then escape from region of the active electrode 11 other than via the saline return channel 18. Any saline which escapes transversely beyond the exterior shaft falls away from the current path, and so is not heated. The priority is, therefore, to ensure that the hottest saline is removed. As the thermal gradient is at a maximum adjacent to the active electrode 11 this is the most appropriate exhaust point for the saline. It is for this reason that the saline is exhausted through the cylindrical portion 15a of the insulator/spacer 15.

Another important consideration in deciding the point of saline evacuation is the potential for blockage of the exhaust path. This could occur when cutting or vaporising tissue in such a way as to free small tissue particles which could easily block the exhaust. The exhaust point is, therefore, selected to be at the highest energy density point on the active electrode 11. This measure ensures that any tissue approaching the exhaust point is instantly vaporised into solution, thereby avoiding the potential for blockage.

Another significant advantage of ensuring a high degree of suction during tissue removal by vaporisation, is that any smoke which has not been absorbed by the saline is also evacuated. This is important, because smoke is capable of transmitting viable biological particles, and this could lead to infection.

As mentioned above, the power threshold for vaporisation is not well defined. If the instrument E1 were operating in a static conductive medium, then the vaporisation threshold would be well defined by an impedance switching point where the electrode impedance suddenly rises as a result of vapour pockets forming around the active electrode 11. The threshold is normally dependent upon the dissipation mechanism of the saline. In a static environment, the dissipation mechanism is predominantly by convection currents within the saline. Under these circumstances, the power threshold for vaporisation is defined by the input power into the electrode active region being in excess of the dissipation from the saline. However, in the embodiment, described above, the saline around the active electrode 11 is continually refreshed. If it were not, then the only dissipation mechanism would be by latent heat of vaporisation, and the saline would quickly evaporate. By providing a flow, the threshold power level is increased. However, the threshold power level is dependent on the saline refresh rate at the very periphery of the active electrode 11. The refresh rate at this boundary layer can be modified by altering the surface finish of the active electrode 11. For example, if the active electrode 11 had a smooth surface, then saline would be rapidly refreshed, as a rapid flow rate would be established. However, as the active electrode 11 has an irregular finish, the refresh rate of pockets within the irregular surface is diminished. Thus, the irregular surface traps saline (or at least delays the refresh), and so absorbs more power before being replaced. In other words, the power threshold is decreased by the irregular active electrode surface. This is a highly desirable property, as the electrode power requirement drops substantially without adversely effecting tissue performance. The threshold power is further reduced because the active electrode is constructed so as to provide a capillary action. Thus, even in the vaporised state, the active electrode 11 is intermittently wetted. By ensuring that this wetting wets the entire active electrode 11 by capillary action, there is a continual source of vapour which minimises the intermittent wetting, and so further reduces the power demand.

To vaporise tissue, it is necessary for the saline being fed from the channel 17 to be in contact with the tissue, as well as with the active electrode 11. The saline, therefore, has to form a constant drip enveloping the active electrode 11. The tip of the active electrode 11 is, therefore, designed so that the saline and the active electrode simultaneously contact tissue regardless of angle. If the flow of saline from the channel 17 to the active electrode 11 were completely annular, saline could flow from one side to the other, in which case the active electrode could be only partially enveloped. It is to prevent this, that the annular channel 17 is segmented by the wings 15b so as to ensure a saline flow on the uppermost surface. This also improves the adherence of the incoming saline by increasing the capillary action.

When the tip of the active electrode 11 comes into contact with the tissue, the region touching the tissue suddenly loses its ability to dissipate power via the saline. Whilst the return path is made up of a flow of saline, the tissue has no mechanism for power dissipation and therefore quickly heats up to the point where it is vaporised.

The effectiveness of the instrument in vaporising tissue is dependent on the ratio between the supported 'drip' and the length of the active electrode 11. A longer active electrode 11 is the most demanding, as the ability to maintain a constant 'drip' is reduced. However, once the active electrode 11 has vaporised a pocket within the tissue, so that the return electrode 12 is closer to the tissue surface, vaporisation becomes easier, as there is a smaller voltage drop across the saline, simply because it forms a smaller part of the electrical circuit.

By varying the output of the generator 1, the instrument E1 can also be used for desiccation (coagulation). In this case, the generator is controlled so that small vapour bubbles form on the surface of the active electrode 11, but insufficient vapour is produced to provide a vapour bubble (pocket) surrounding the active tip of the electrode 1, the vapour bubble being essential for tissue removal by vaporisation.

The generator 1 is controlled in such a manner that it has respective output ranges for tissue desiccation and for tissue removal by vaporisation. The former range is from 150 volts to 200 volts, and the latter range is from 250 volts to 600 volts, the voltages being peak voltages. In the vaporisation mode, the generator 1 is controlled in such a manner as to prevent the active electrode 11 overheating. This requires a reduction in the output voltage of the generator 1 once a vapour pocket has been established. The generator 1 and its control means are described in greater detail in the specification of our co-pending British patent application 9604770.9.

The coagulation from this electrode is vastly superior to any conventional bipolar electrode. The reasons are two fold. Firstly, the coagulation mechanism is not merely by electrical current in the tissue, but is also due to the heated saline. Secondly, under normal circumstances, the weakest link in providing electrical power to the tissue is the electrode/tissue interface, as this is the point of highest power density, and so imposes a power limit. If too high a power level is attempted, the tissue at the interface quickly desiccates, far faster than the larger cross-section of tissue forming the remaining circuit. If a lower power is selected, the interface can dissipate the temperature rise by mechanisms other than evaporation. Consequently, the interface remains intact longer, and so a greater depth of effect can be achieved. In this embodiment, the electrical interface is much stronger by virtue of the saline, and it is not possible completely to desiccate the target tissue. Thus, power can be delivered at a higher rate and for a longer period, resulting in a depth of effect which is purely time and power related.

Figure 3:
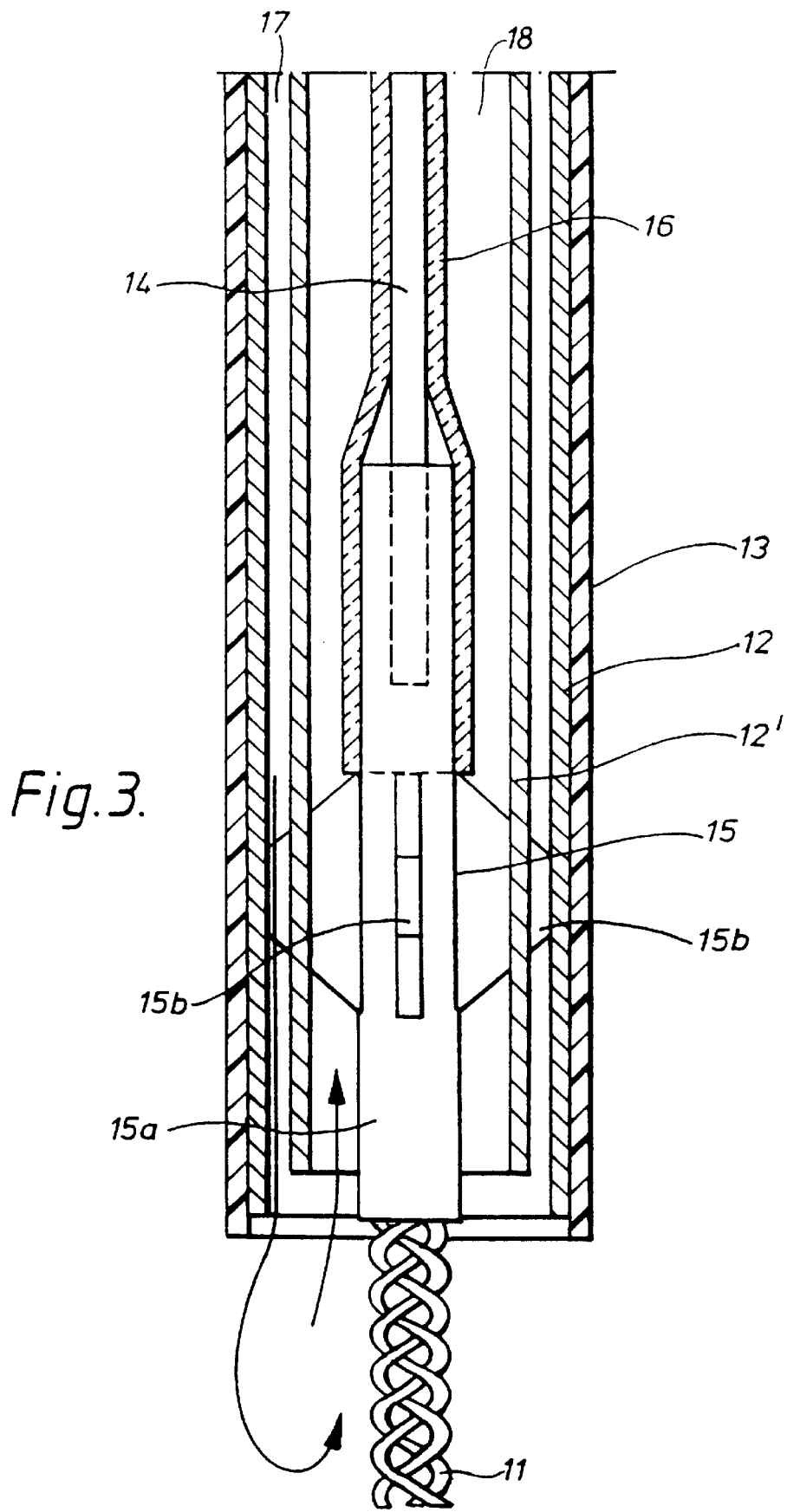
FIG. 3 is a schematic longitudinal sectional view of a second form of electrosurgical instrument for use with the apparatus of FIG. 1.

FIG. 3 shows the distal end of the second form of electrosurgical instrument. This instrument is a modification of that shown in FIG. 2, so like reference numerals will be used for like parts, and only the modifications will be described in detail. The main modification is that the instrument of FIG. 2 includes two co-axial, tubular return electrodes 12 and 12', the return electrode 12' being slightly shorter than the return electrode 12 and being positioned therewithin. The annular gap between the two return electrodes 12 and 12' constitute the saline feed channel 17, and the saline return channel 18 is constituted by the annular gap between the return electrode 12' and the central construction constituted by the cylindrical portion 15a of the insulator/spacer 15 and the tube 16. The tube 16 is also modified to form a friction fit around both the proximal end of the cylindrical portion 15a of the insulator/spacer 15 and the active conductor 14.

The advantage of the instrument of FIG. 3 is that, when it is used to create vaporised pockets in a tissue surface (for example in an embedded tumour) there is less chance of the return path of saline to the saline return channel 18 being blocked. Thus, with the embodiment of FIG. 2 when a vapour pocket is created, some saline forming the conduction path between the active electrode 11 and the return electrode 12 can escape due to tissue obstructing the entrance to the return channel 18. This saline can be of a sufficiently high temperature to cause some peripheral tissue blanching. As tissue blanching is dependent upon the size of the instrument, the instrument of FIG. 2 should have small dimensions, so that the amount of peripheral blanching can be maintained at acceptable levels. With the embodiment of FIG. 3, on the other hand, the return path of saline from the active electrode 11 to the return channel 18 will then never be obstructed by tissue. Moreover, when the conduction path between the active electrode 11 and the return electrode 12 is obstructed, the portion of saline obstructed from the active electrode 11 has a reduced power dissipation. This reduced dissipation arises from the fact that both inlet and output saline are connected to the return channel 18, so the impedance is lower to the extent that the majority of power dissipation then occurs in the obstructing tissue.

The instrument of FIG. 3 is, therefore, less suitable for miniaturisation than that of FIG. 2, due both to the extra tubing (the extra return electrode 12') and the aspect ratio of the tip (i.e. the active electrode 11 cannot protrude as much per diameter due to the saline exhaust being stepped further back). This exhaust has to be positioned further back, as it is passed through the second return electrode 12'. If it were not so positioned, it would cause too great a power distribution over the length of the active electrode 11.

The exhaust saline from the instrument of FIG. 3 may also contain tissue particulates. As the exhaust path does not necessarily pass through a vaporising region, this imposes a limit to the minimum size of this version of the instrument, due to the potential for blockage of the exhaust path.

The best vaporising performance for each of the instruments described above is when the active electrode 11 is designed to trap, or at least interrupt, saline flow. The reason for this is quite simple, namely that the longer saline can be kept in close proximity to the active electrode 11 the more power it absorbs, and hence the greater the propensity to form a vapour. Wire or hollow forms of active electrode are, therefore, the most effective. It would, for example, be possible to replace the twisted form of wire form of active electrode by an active electrode in the form of a coil. It would also be possible to improve vaporisation by partially obscuring the active electrode/saline interface by masking with sprayed ceramic, sprayed ceramic being deposited at a particulate non-uniform coating.

The instruments described above have a number of advantages namely:

1. Each can provide a monopolar like action with only one electrode (the active electrode 11) in direct tissue contact;
2. Each provides immediate tissue debulking (vaporisation) in a manner similar to that obtained with laser instruments;
3. RF current is confined to the area of treatment, thereby reducing collateral or deep thermal effects, and eliminating remote burns;
4. There is minimal smoke when cutting or vaporising, due to the cooling, condensing and dissolving effects of the surrounding saline. Any smoke produced is rapidly removed due to the suction adjacent to the active electrode 11;
5. As the current path within the electrode assembly is bidirectional, there is minimal capacitive coupling at any electrode entry points;
6. The saline provides an excellent active electrode/tissue interface which preserves current flow for a controlled depth of coagulation, this being dependent purely on power and application time.
7. The saline connection prevents high impedance conditions which could cause significant carbonization which is known to be detrimental to tissue healing, and increases the risk of adhesion formation;
8. The excellent low impedance active electrode/tissue interface permits the use of much higher powers for rapid effects. This is particularly useful for quick non-carbonizing coagulation; and
9. Much higher power levels are supported than for conventional bipolar electrosurgery. In practice, conventional bipolar electrosurgery is only effective to a limit of 40 W or 50 W, as higher power levels result in overheating and carbonization. With the electrode configuration of FIGS. 2 and 3 power levels in excess of 200 W can be supported.

It will be apparent that modifications could be made to the instruments described above. Thus, the active electrode 11 could be of any other suitable form, such as a needle electrode or a hollow, perforated part-spherical electrode made, for example, of platinum/iridium, and the insulator/spacer 15 would be made of silicone rubber or glass. It would also be possible to replace saline as the conductive medium with a conductive gas such as argon. In this case, the argon would need to be pumped to the region of the active electrode 11 through the channel 17, and there would be no need to remove the argon via the return channel 18, there being no danger of collateral tissue damage from hot argon. In this case also, a modified form of RF generator would be needed. The entire electrode assembly could be constructed as a flexible or rigid assembly, and could also incorporate means for steering or manipulating the active tip, or insertion into tissue.

We claim:

1. An electrosurgical instrument for the treatment of tissue in the presence of an electrically-conductive fluid, the instrument comprising an instrument shaft and an electrode assembly at one end of the shaft, the electrode assembly comprising:

a tissue treatment electrode, a return electrode, and an insulation member which electrically insulates the return electrode from the tissue treatment electrode, the tissue treatment electrode being exposed at the extreme distal end of the instrument, and the return electrode having a fluid contact surface axially spaced from the exposed end of the tissue treatment electrode by the insulation member so that, in use, the return electrode does not contact the tissue to be treated, wherein the instrument further comprises, a feeder for feeding cool electrically-conductive fluid to the region of the exposed end of the tissue treatment electrode in such a manner as to define, in use, a conductive fluid path that completes an electrical circuit between the tissue treatment electrode and the return electrode, and an extractor for removing heated electrically-conductive fluid from the region of the exposed end of the tissue treatment electrode.

2. An electrosurgical instrument as claimed in claim 1, wherein the feeder is such that the maximum flow rate of electrically-conductive fluid is 0.32 cc/s per 100 watts of electric power applied to the electrode assembly.

3. An electrosurgical instrument as claimed in claim 1 wherein the treatment electrode is made of twisted noble metal.

4. An electrosurgical instrument as claimed in claim 1 wherein the treatment electrode is made of wire.

5. An electrosurgical instrument as claimed in claim 1 wherein the treatment electrode is hollow.

6. An electrosurgical instrument as claimed in claim 1, wherein the return electrode is a tubular member which is coated with an insulating sheath, the coated return electrode constituting the instrument shaft.

7. An electrosurgical instrument as claimed in claim 6, wherein an inner surface of the tubular member comprises the return electrode.

8. An electrosurgical instrument as claimed in claim 6, wherein the tubular member is made of stainless steel.

9. An electrosurgical instrument as claimed in claim 6, wherein the tissue treatment electrode is supported centrally within the tubular member by an insulating spacer.

10. An electrosurgical instrument as claimed in claim 9, wherein the insulating spacer is made of a ceramic material, silicone rubber or glass.

11. An electrosurgical instrument as claimed in claim 9, further comprising a tube extending proximally of the spacer.

12. An electrosurgical instrument as claimed in claim 11, wherein the fluid feed channel is constituted by the annular space between the return electrode and the tube, and the fluid return channel is constituted by the interior of the tube and aperture means extending through the spacer.

13. Electrosurgical apparatus comprising a radio frequency generator and an electrosurgical instrument for the treatment of tissue in the presence of an electrically-conductive fluid medium, wherein the electrosurgical instrument comprises an instrument shaft and an electrode assembly at one end of the shaft, the electrode assembly comprising:
   a tissue treatment electrode,
   a return electrode, and
   an insulation member which electrically insulates the return electrode from the tissue treatment electrode,
   the tissue treatment electrode being exposed at the extreme distal end of the instrument, and
   the return electrode having a fluid contact surface axially spaced from the exposed end of the tissue treatment electrode by the insulation member so that, in use, the return electrode does not contact the tissue to be treated,
   wherein the instrument further comprises feed means for feeding cool electrically-conductive fluid to the region of the exposed end of the tissue treatment electrode in such a manner as to define, in use, a conductive fluid path that completes an electrical circuit between the tissue treatment electrode and the return electrode, and
   an extractor for removing heated electrically-conductive fluid from the region of the exposed end of the tissue treatment electrode.

14. An electrosurgical instrument as claimed in claim 13, wherein the surface of the exposed end of the tissue treatment electrode is not smooth, whereby electrically-conductive fluid is trapped by said irregular surface, thereby reducing the rate of which cool electrically-conductive fluid is fed to the region of the exposed end, and enabling the electrically-conductive fluid in said region to absorb more power before being replaced by fresh electrically-conductive fluid.

15. An electrosurgical instrument as claimed in claim 13, wherein the extractor comprises a fluid return channel and has sufficient power to remove electrically-conductive fluid from said region at a rate faster than that at which the feeder feeds electrically-conductive fluid thereto, thereby ensuring that heated electrically-conductive fluid can escape from said region only via the fluid return channel and that smoke and other by-products of tissue vaporization are removed from said region via the fluid return channel.

16. An electrosurgical instrument as claimed in claim 13, wherein the feed means comprises a fluid feed channel segmented by a plurality of wings which ensure adherence of the fed cool electrically-conductive fluid to the tissue treatment electrode so as to encourage capillary flow of said fluid along said tissue treatment electrode, thereby ensuring that, even when the electrode assembly is powered so as to vaporize electrically-conductive fluid in the region of the exposed end of the tissue treatment electrode, the tissue treatment electrode is intermittently wetted, thereby ensuring that there is a continual score of vapor and a reduction in the power demand.

17. An electrosurgical instrument as claimed in claim 13, wherein the feed means is such that the maximum flow rate of electrically-conductive fluid is 0.32 cc/s per 100 watts of electric power applied to the electrode assembly.

18. Apparatus as claimed in claim 13, wherein the radio frequency generator includes control means for varying the output power delivered to the electrodes.

19. Apparatus as claimed in claim 18, wherein the control means is such as to provide output power in first and second output ranges, the first output range being for powering the electrosurgical instrument for tissue desiccation, and the second output range being for powering the electrosurgical instrument for tissue removal by cutting or vaporisation.

20. Apparatus as claimed in claim 19, wherein the first output range is from about 150 volts to 200 volts, and the second output range is from about 250 volts to 600 volts, the voltages being peak voltages.

21. An electrosurgical instrument for the treatment of tissue in the presence of an electrically-conductive fluid, the instrument comprising an instrument shaft and an electrode assembly at one end of the shaft, the electrode assembly comprising
   a tissue treatment electrode,
   a return electrode, and
   an insulation member which electrically insulates the return electrode from the tissue treatment electrode,
   the tissue treatment electrode being exposed at the extreme distal end of the instrument, and
   the return electrode having a fluid contact surface spaced from the exposed end of the tissue treatment electrode by the insulation member,
   wherein the instrument further comprises, a feeder for feeding cool electrically-conductive fluid to the region of the exposed end of the tissue treatment electrode in such a manner as to define, in use, a conductive fluid path that completes an electrical circuit between the tissue treatment electrode and the return electrode, and
   an extractor for removing heated electrically-conductive fluid from the region of the exposed end of the tissue treatment electrode, and
   wherein the return electrode is a tubular member which is coated with an insulating sheath, the coated return electrode constituting the instrument shaft, and further comprising
   a second return electrode, the second return electrode being constituted by a second tubular member positioned concentrically within the first-mentioned tubular member.

22. An electrosurgical instrument as claimed in claim 21 further comprising a tube extending proximally of a spacer supporting the tissue treatment electrode within the first-mentioned tubular member, the fluid feed channel comprising the annular space between the two tubular members, and the fluid return channel comprising the annular space between the second tubular member and the tube.

23. An electrosurgical instrument as claimed in claim 22, wherein the distal end of the second tubular member is set back proximally with respect to the distal end of the first-mentioned tubular member, thereby reducing the potential for the flow of heated electrically-conductive fluid into the fluid return channel being blocked by excised tissue pieces.

24. An electrosurgical instrument for the treatment of tissue in the presence of an electrically-conductive fluid, the instrument comprising an instrument shaft and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a fluid contact surface spaced from the exposed end of the tissue treatment electrode by the insulation member, wherein the instrument further comprises, a feeder for feeding cool electrically-conductive fluid to the region of the exposed end of the tissue treatment electrode in such a manner as to define, in use, a conductive fluid path that completes an electrical circuit between the tissue treatment electrode, and the return electrode, and an extractor for removing heated electrically-conductive fluid from the region of the exposed end of the tissue treatment electrode, and wherein the feeder is such that the maximum flow rate of electrically-conductive fluid is 0.32 cc/s per 100 watts of electric power applied to the electrode assembly.

25. An electrosurgical instrument as claimed in claim 24 wherein the extractor comprises a fluid return channel formed within the instrument shaft, and means for applying suction to the proximal end of the fluid return channel.

26. An electrosurgical instrument as claimed in claim 25, wherein the fluid return channel has a distal end which is spaced proximally from the exposed end of the tissue treatment electrode, thereby reducing the potential for the flow of heated electrically-conductive fluid into the fluid return channel being blocked by excised tissue pieces at said distal end.

27. An electrosurgical instrument as claimed in claim 24 wherein the extractor comprises a fluid return channel formed within the instrument shaft, and means for applying suction to the proximal end of the fluid return channel.

28. An electrosurgical instrument as claimed in claim 27, wherein the fluid return channel has a distal end, the exposed end of the tissue treatment electrode has a highest energy density point, and the distal end of the fluid return channel is adjacent to the highest energy density point of the exposed end of the tissue treatment electrode, whereby small tissue particles are vaporized, thereby avoiding the potential for blockage of said distal end of the fluid return channel.

29. An electrosurgical instrument as claimed in claim 27, wherein the fluid return channel has a distal end which is spaced proximally from the exposed end of the tissue treatment electrode, thereby reducing the potential for the flow of heated electrically-conductive fluid into the fluid return channel being blocked by excised tissue pieces at said distal end.

30. An electrosurgical instrument as claimed in claim 27, wherein the fluid return channel has a distal end which is adjacent to the exposed end of the tissue treatment electrode, whereby the electrically-conductive fluid is removed via the fluid return channel.

31. An electrosurgical instrument as claimed in claim 32, wherein the fluid feed channel is such that electrically-conductive fluid is fed to the region of the exposed end of the tissue treatment electrode in a non-annular flow.

32. An electrosurgical instrument as claimed in claim 27, wherein the feeder comprises a fluid feed channel formed within the instrument shaft.

33. An electrosurgical instrument as claimed in claim 32, wherein the fluid feed channel is positioned around the fluid return channel.

34. An electrosurgical instrument as claimed in claim 32, wherein the fluid feed channel is provided with at least one wing for affecting the flow of the electrically-conductive fluid to provide a non-annular flow of said fluid.

35. Electrosurgical apparatus comprising a radio frequency generator and an electrosurgical instrument for the treatment of tissue in the presence of an electrically conductive fluid medium, wherein the electrosurgical instrument comprises an instrument shaft and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a fluid contact surface spaced from the exposed end of the tissue treatment electrode by the insulation member, wherein the instrument further comprises feed means for feeding cool electrically-conductive fluid to the region of the exposed end of the tissue treatment electrode in such a manner as to define, in use, a conductive fluid path that completes an electrical circuit between the tissue treatment electrode and the return electrode, and an extractor for removing heated electrically-conductive fluid from the region of the exposed end of the tissue treatment electrode, and wherein the extractor comprises a fluid return channel and has sufficient power to remove electrically-conductive fluid from said region at a rate faster than that at which the feeder feeds electrically-conductive fluid thereto, thereby ensuring that heated electrically-conductive fluid can escape from said region only via the fluid return channel, and that smoke and other by-products of tissue vaporization are removed from said region via the fluid return channel.

36. Electrosurgical apparatus comprising a radio frequency generator and an electrosurgical instrument for the treatment of tissue in the presence of an electrically conductive fluid medium, wherein the electrosurgical instrument comprises an instrument shaft and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a fluid contact surface spaced from the exposed end of the tissue treatment electrode by the insulation member, wherein the instrument further comprises feed means for feeding cool electrically-conductive fluid to the region of the exposed end of the tissue treatment electrode in such a manner as to define, in use, a conductive fluid path that completes an electrical circuit between the tissue treatment electrode and the return electrode, and an extractor for removing heated electrically-conductive fluid from the region of the exposed end of the tissue treatment electrode, wherein the feed means comprises a fluid feed channel segmented by a plurality of wings which ensure adherence of the fed cool electrically-conductive fluid to the tissue treatment electrode so as to encourage capillary flow of said fluid along said tissue treatment electrode, thereby ensuring that, even when the electrode assembly is powered so as to vaporize electrically-conductive fluid in the region of the exposed end of the tissue treatment electrode, the tissue treatment electrode is intermittently wetted, thereby ensuring that there is a continual source of vapor and a reduction in the power demand.

37. Electrosurgical apparatus comprising a radio frequency generator and an electrosurgical instrument for the treatment of tissue in the presence of an electrically conductive fluid medium, wherein the electrosurgical instrument comprises an instrument shaft and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a fluid contact surface spaced from the exposed end of the tissue treatment electrode by the insulation member, wherein the instrument further comprises feed means for feeding cool electrically-conductive fluid to the region of the exposed end of the tissue treatment electrode in such a manner as to define, in use, a conductive fluid path that completes an electrical circuit between the tissue treatment electrode and the return electrode, and an extractor for removing heated electrically-conductive fluid from the region of the exposed end of the tissue treatment electrode, and wherein the feeding means is such that the maximum flow rate of electrically-conductive fluid is 0.32 cc/s per 100 watts of electric power applied to the electrode assembly.

* * * * *